United States Patent [19]
Kimm et al.

[11] Patent Number: 5,390,666
[45] Date of Patent: * Feb. 21, 1995

[54] SYSTEM AND METHOD FOR FLOW TRIGGERING OF BREATH SUPPORTED VENTILATION

[75] Inventors: Gardner J. Kimm, Carlsbad; Glen N. Gee, Encinitas; Paul J. Fennema, Fallbrook; Warren G. Sanborn, Escondido, all of Calif.

[73] Assignee: Puritan-Bennett Corporation, Carlsbad, Calif.

[*] Notice: The portion of the term of this patent subsequent to Nov. 10, 2009 has been disclaimed.

[21] Appl. No.: 161,177

[22] Filed: Dec. 3, 1993

Related U.S. Application Data

[63] Continuation of Ser. No. 940,463, Sep. 4, 1992, abandoned, which is a continuation-in-part of Ser. No. 522,383, May 11, 1990, Pat. No. 5,161,525.

[51] Int. Cl.6 .................. A61M 16/00; A62B 7/04; F16K 31/02; F16K 31/26
[52] U.S. Cl. .................. 128/204.26; 128/204.23
[58] Field of Search .................. 128/204.18, 204.21, 128/204.23, 204.26

[56] References Cited

U.S. PATENT DOCUMENTS

| | | | |
|---|---|---|---|
| 3,741,208 | 6/1973 | Jonsson et al. | 128/204.23 |
| 3,905,362 | 9/1975 | Eyrick et al. | 128/204.18 |
| 3,927,327 | 8/1976 | Ernst et al. | 128/204.21 |
| 3,961,627 | 6/1976 | Ernst et al. | 128/204.21 |
| 4,281,651 | 8/1981 | Cox | 128/204.23 |
| 4,421,113 | 12/1983 | Gedeon et al. | 128/204.23 |
| 4,527,557 | 7/1985 | De Vries et al. | 128/205.24 |
| 4,577,975 | 7/1987 | Edgar et al. | 128/204.23 |
| 4,686,974 | 8/1987 | Sato et al. | 128/204.23 |
| 4,776,333 | 10/1988 | Miyamae | 128/204.21 |
| 4,823,788 | 4/1989 | Smith et al. | 128/205.24 |
| 4,928,684 | 5/1990 | Braitenfelder et al. | 128/204.21 |
| 5,161,525 | 11/1992 | Kimm et al. | 128/204.23 |

FOREIGN PATENT DOCUMENTS

| | | | |
|---|---|---|---|
| 0343542A2 | 5/1989 | European Pat. Off. | |
| 0402951 | 12/1990 | European Pat. Off. | 128/204.23 |

OTHER PUBLICATIONS

Flow-By Option 50, pp. 1-6, Puritan-Bennett Corporation.
7200a Option #50 Flow-By, Puritan-Bennett Corporation.

*Primary Examiner*—Kimberly L. Asher
*Attorney, Agent, or Firm*—Fulwider Patton Lee & Utecht

[57] ABSTRACT

The method for flow triggering breath supported ventilation is accomplished by providing a system comprising a source of a predetermined, preinspiratory, constant flow of breathing gas and connecting such to a patient breathing attachment. One or more flow sensors measure the gas flow rate in a flow path communicating with the patient breathing attachment, determining when inhalation from the flow path has occurred. Breath support is generated in the delivered gas flow in response to inhalation by the patient, and the predetermined, preinspiratory, continuous flow of breathing gas is reestablished prior to the patient's next inspiratory effort. In combination with various types of breath support, the flow triggering strategy of the invention offers significant improvements in providing breath support to patients having weakened respiratory capabilities.

15 Claims, 5 Drawing Sheets

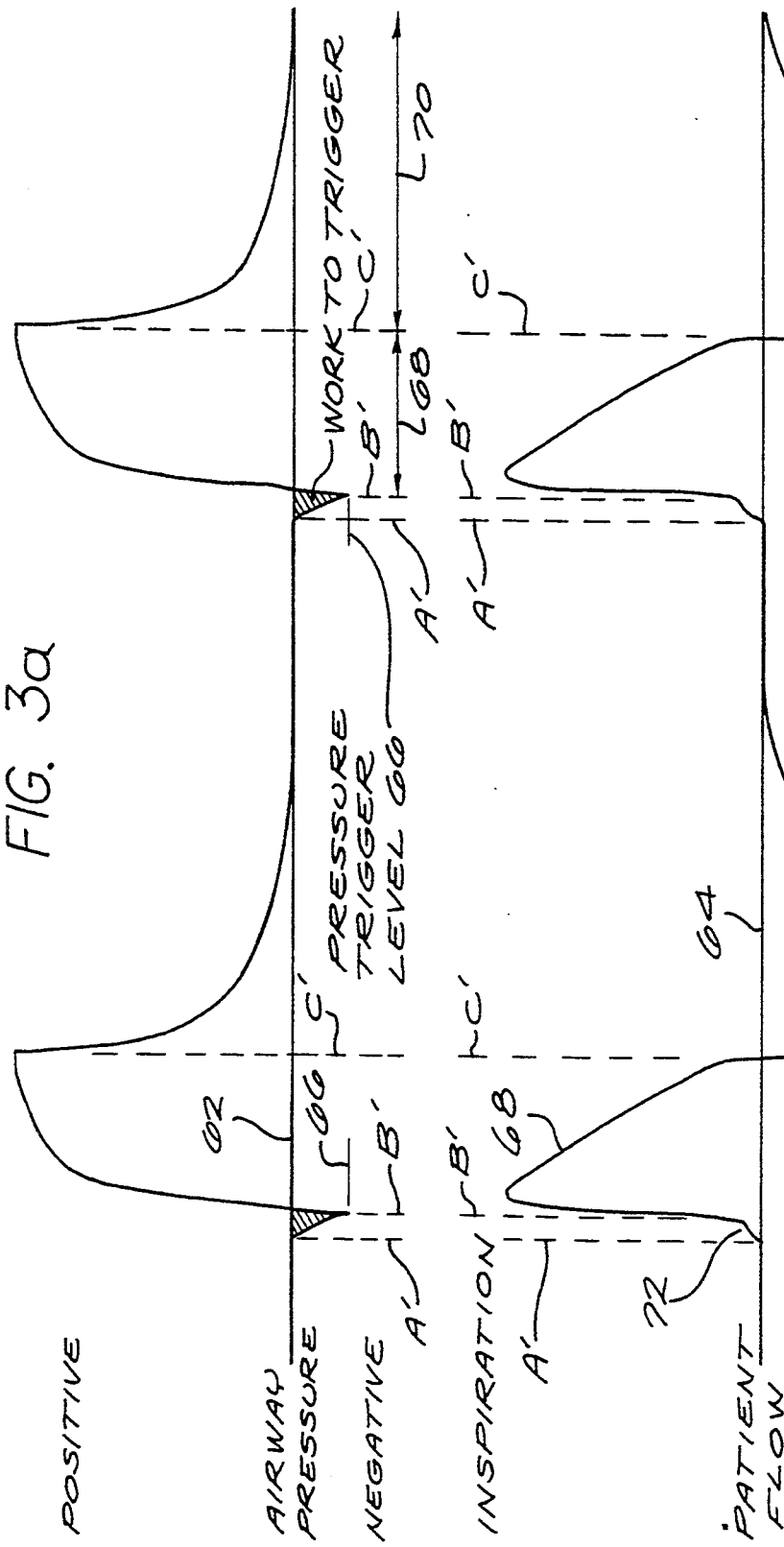

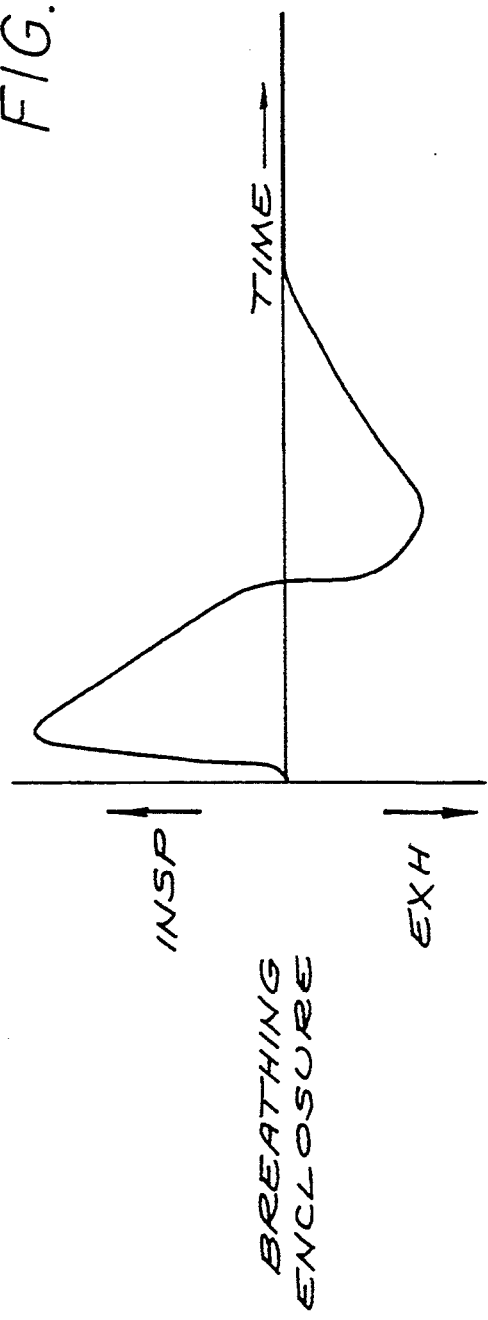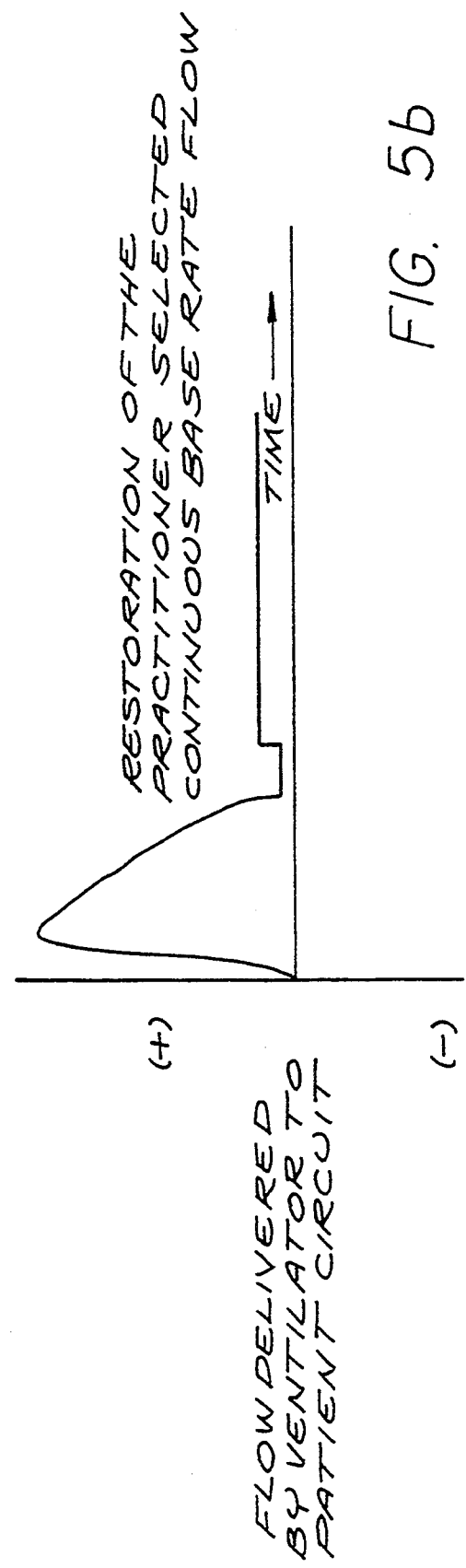

SYSTEM AND METHOD FOR FLOW TRIGGERING OF BREATH SUPPORTED VENTILATION

This application is a continuation of application Ser. No. 07/940,463, filed Sept. 4, 1992, now abandoned; which is a continuation-in-part of 07/522,383, filed May 11, 1990, now U.S. Pat. No. 5,161,525.

BACKGROUND OF THE INVENTION

1. Field of the Invention

This invention relates generally to breathing ventilators, and more particularly relates to a pneumatically driven, electronically controlled, ventilator system for providing breathing gas to a patient, and a system and method for flow triggering of various types of patient initiated ventilator supported breaths.

2. Description of Related Art

Breathing ventilator systems conventionally provide a breathing gas for either non-pressure supported breaths during inspiration at a pressure level typically no more than 2 cm. of water above or below the pressure baseline, or pressure supported breaths of breathing gas at a support pressure during inspiration as high as 70 to 100 cm. of water. Pressure support is also known in the art by other names, such as inspiratory assist, pressure assist, or inspiratory pressure assist. Such breathing gas is often supplemented with a higher proportion of oxygen than is found in the ambient atmosphere. The respiration work performed by a patient on a ventilator may be divided into two major components: the work to initiate a breath and the work to sustain a breath. During this century, many novel and efficacious techniques have been devised to supply breathing gas to patients, but the purpose of the great majority of such techniques has been to improve patient efforts to breath by reducing the work to sustain a breath, once a ventilator system has been triggered by a patient's inspiratory effort. Relatively few improvements have been made in reduction of the patient's inspiratory work required to trigger a ventilator system to assist the patient's breathing. It is desirable to reduce the effort expended by the patient in each of these phases, since a high level of such effort can cause further damage to a weakened patient or be beyond the capabilities of small or disabled patients. As discussed below, a variety of strategies and systems have been developed to address these problems, but important issues still remain in the reduction of work demanded by ventilators to command and sustain a breath.

A patient whose breathing is being supported by a ventilator system typically receives breathing gas through a patient circuit. The patient circuit generally consists of two flexible conduits connected to a fitting called a patient wye. The free ends of the conduits are attached to the ventilator so that one conduit receives breathing gas from the ventilator's pneumatic system, and the other conduit returns gas exhaled by the patient to the ventilator. The volume of the exhaled gas may then be measured in a spirometer before it finally exits through an exhalation valve. The wye fitting is typically connected to the patient's breathing attachment or enclosure, which conducts breathing gas into the lungs, and exhaled gas from the lungs to the an exhalation branch of the patient circuit. The pneumatic system at the inspiratory end of the patient circuit is typically closed before a breath, and the exhalation valve at the exhalation end of the patient circuit is typically preceded by a one way valve, to prevent gas from flowing retrograde in the exhalation branch of the patient circuit.

Ventilators presently known in the art are commanded to deliver inspiration support, or a specific flow of breathing gas during an inspiratory phase of breathing, based upon a "pressure trigger" as described below. With such a system, when a patient's spontaneous inspiratory effect withdraws a small volume of gas from the breathing gas circuit, the corresponding drop in pressure in the closed ventilator circuit is monitored, and when a predetermined triggering pressure threshold is reached, a control mechanism causes the ventilator's pneumatic system to deliver breathing gas at the desired pressure or flow rate. This activation of the ventilator cycle by means of a patient induced negative pressure may be termed "pressure triggering". A certain amount of lag time and associated negative pressure always occurs between the onset of inspiratory effort and the time that the gas pressure or flow reaches the patient's airway. This lag time (or delay) is generally referred to as a ventilator's response time, and commonly occupies a small but significant portion of a patient's total inspiration time.

Pressure triggering of inspiration support relies upon the transmission of pressure waves throughout the closed breathing gas circuit. These pressure waves travel to the pressure sensor at the speed of sound in the gas, which is approximately 1 millisecond per foot. Although electronic processing of pressure wave signals can occur very rapidly, due to factors inherent in ventilator design, patient inspiration effort can typically continue for as long as 40 to 50 milliseconds without ventilator assistance. Under the conventional pressure triggering ventilation schemes, the pressure drop, which a patient is required to create in a closed breathing gas circuit in order to trigger a breath, can require a significant expenditure of energy by the patient. This imposed work on the patient can be detrimental in that respiratory muscles already fatigued by an operation or other patient condition may fatigue. In addition, this respiratory work may be beyond the capability of some patients, such as neonates, small children, or patients severely weakened by trauma or disease, resulting in the inability of the patient to rhythmically trigger the inspiratory support of the ventilator. If this process continues to worsen, the patient may experience failure or severe compromise of the ventilation process. Thus, the ventilator response time, plus the lag time associated with pressure triggering, can result in a significant expenditure of work by the patient in order to command a breath from the ventilator.

The signal to cycle on the ventilator to deliver pressure or volume support of patient breaths by monitoring flow in the patient's breathing gas circuit or inside the ventilator has recently been accomplished in the context of a closed breathing gas circuit. In such a system, a single flow sensor is typically positioned inside the ventilator to monitor the flow of gas that a patient withdraws from the closed system and trigger a pressure or volume based breath when the patient's inspiratory flow equals a certain predetermined level. However, such a closed system, flow based trigger is not an improvement over a closed system pressure triggered arrangement, because all of the same delays and work required of the patient are present. In addition, a significant negative pressure drop is still required to start the breath, and there is no continuous flow to support the earliest phase of the breath. Therefore, the patient must overcome the substantial inertia of the breath triggering process. It is commonly recognized that the patient generates an isometric effort when triggering a ventilator. For some patients, this creates no unwanted consequences, whereas for other patients, particularly those who are smaller or weaker, and severely compromised, the triggering effort unnecessarily burdens their respiratory muscles.

In order to decrease the work of sustaining the flow of a breath after it has been initiated, thereby reducing the work required of the patient, breathing ventilator systems conventionally provide a breathing gas for non-pressure supported breaths during inspiration at a pressure level typically no more than 2 cm. of water above or below the pressure baseline. In pressure supported systems, breaths of breathing gas are delivered at a pressure support level during inspiration as high as 70-100 cm. of water. These higher pressures are used to supplement patient effort, overcome airway resistance, and reduce the work of breathing for the patient. This use of a higher pressure support level can provide enhanced comfort for the patient, and may facilitate the weaning of the patient from the ventilator.

To circumvent or overcome the problems associated with breath triggering in the context of a closed ventilator circuit, a continuous flow system may be employed. To ensure that the patient receives a flow of breathing gas immediately upon initiation of an inspiratory effort and with the appropriate oxygen concentration, a flow regulator is positioned at the inlet of the breathing gas circuit to deliver a constant gas flow in excess of the peak flow demand expected from the patient. This "continuous flow" approach eliminates the ventilator's delay time and significantly reduces the negative pressure work associated with closed ventilator systems.

An advantage of the continuous gas flow (available in an open breathing gas system) is that a patient's inspiratory effort results in an immediate flow of breathing gas into the patient's trachea, without the delays and with less negative pressure work inherent in closed ventilator systems. Thus, it would be desirable to provide breathing support to a patent in an initially, open continuous flow system rather than from a closed breathing gas system. It would also be desirable to provide a method and system for triggering a variety of ventilator supported breaths which can be made to be more sensitive than previous pressure based strategies.

From the above, it is clear that it would be desirable to combine the advantages of flow sensing and triggering in a functionally open, breathing gas circuit with various types of breathing support for the purpose of enabling the ventilator to reduce significantly both the work of breathing during the earliest phase as well as the patient's breathing work during the later phases of the inspiratory effort. The present invention accomplishes these goals.

SUMMARY OF THE INVENTION

An excessively high expenditure of energy by the patient, early in the inspiratory process, can be detrimental to the patient. Patients may fatigue under these imposed workloads, leading to further respiratory distress and/or failure. The required energy expenditure can also create difficulties in weaning the patient from the ventilator, leading to patients who become ventilator dependent. Thus, reducing the energy expenditure while breathing on a mechanical ventilator is advantageous for the patient.

The energy expended while breathing on a mechanical ventilator may be divided into two components. The first of such components is the energy required to trigger the ventilator to initiate inspiratory support. The second component is the energy required to maintain gas flow once the inspiration has been initiated. The use of flow triggering within the context of a continuous gas flow system minimizes the first component, since a patient has a continuous supply of appropriately mixed gas immediately available from which to draw, essentially eliminating the lag time and minimizing the earliest work of breathing for volume or pressure based, patient initiated breaths. The strategy behind the various support modes of ventilation is to reduce the second component by providing at least a minimum of positive pressure to overcome airway resistance and to supplement patient effort. While each of these techniques is helpful in reducing the work to be performed by the patient on the respirator, it would be desirable to provide a ventilator system that combined these two work reducing concepts, thereby enabling the ventilator to manage all phases of the energy expended by the patient. Such a level of performance is unavailable in current systems.

The present invention provides a system and method of triggering various types of supported breaths for a patient on a ventilation system that is initially open (and is provided with a preinspiratory flow of breathing gas), that is equipped to measure the flow of inhaled gas into the patient, and that triggers the delivery of pressure support when the flow of inhaled gas equals a preset, threshold value of flow. By implementing flow sensing in an open circuit design, in which setting the ventilator establishes a controlled and minimal, preinspiratory, continuous flow of gas in the breathing gas circuit, the ventilator acquires the means to cycle on the pressure support function while eliminating the ventilator's lag time and minimizing the patient's earliest inspiratory efforts. When this method of flow triggering is combined with various types of breath support ventilation, including pressure support, the patient's work of breathing can be managed to virtually any desirable level. An additional benefit provided by flow triggering of breath supported ventilation is the elimination of self-triggering of the ventilator due to leaks in the patient's physiology and/or the breathing gas circuit, without degrading ventilator sensitivity.

Briefly and in general terms, the flow triggering system for delivering breathing gas to a patient of the present invention comprises a source of a preinspiratory, constant flow of breathing gas to a patient breathing attachment, flow sensor means for measuring the rate of gas flow in a ventilation flow path communicating with the patient breathing attachment, means for determining when inhalation from said flow path has occurred, means for generating breath support during the inspiratory phase of the breath in response to inhalation by the patient, and means for reestablishing the constant flow of breathing gas to the patient breathing attachment after the end of the inspiratory phase of the breath support and before the new inspiratory effort begins.

In the preferred embodiment of the system of the invention, a plurality of individual gas sources provide a controlled mixture of breathing gas for breath support. It is preferable to mount flow sensor means in both the flow path to (inspiration) and the flow path from (exhalation) the patient, and measure the flow extracted by the patient as the difference of the two. It is preferred to discontinue breath support at the conclusion of the inspiratory phase of the breath. It is also preferred to reestablish the continuing flow of breathing prior to the patient's next inspiratory effort.

In the preferred method of the invention, the flow triggering of pressure supported ventilation involves the steps of (1) providing a predetermined, preinspiratory, continuous flow rate of breathing gas from a source to the patient breathing attachment, (2) measuring the flow rate in the ventilation flow path due to the patient's inhalation as the difference between flow sensor means placed in the ventilation flow path to and from the patient, (3) generating breath support during the inspiratory phase of the breath when the flow due to inhalation exceeds a predetermined threshold value, and (4) reestablishing the predetermined, continuous flow rate of breathing gas from a source to the patient breathing attachment prior to his/her next respiratory effort. The method further preferably comprises mixing a plurality of individual gases from different sources, and controlling proportions of the mix of gases. It is currently preferred to discontinue breath support when an exhalation effort is detected from a rise in pressure to a threshold value, or when flow declines to below a threshold value.

The approach of the present invention to the combination of flow triggering with breath support provides a spontaneous breath whose work of inspiration can be closely controlled by an appropriate selection of the level of support pressure. The energy required to trigger the breath is minimal due to the flow triggering strategy described in the invention. Once the breath is triggered, the level of breath support in combination with the patient's airway resistance (including that of the artificial airway and lumped chest wall and lung compliance) allows the energy expended throughout the rest of the inspiratory phase to be closely managed. There are also other advantages to flow triggering of breath supported ventilation when used for small children or infants, where the high sensitivity of triggering is a distinct advantage, since small patients find pressure triggering more strenuous due to their weaker respiratory systems. In addition, the dead space that must be evacuated for pressure triggering is also more difficult for patients with small lungs. Very often, patients who cannot successfully pressure trigger a ventilator can flow trigger the ventilation process.

These additional advantages of the present invention derive in part from the physics of the flow triggering strategy. Before a patient initiates an inspiratory effort, a predetermined, preinspiratory controlled, and measured flow of breathing gas is delivered into the patient's breathing gas circuit. This breathing gas (air or oxygen enriched air) flows past the patient wye, which is connected to the patient's breathing attachment (artificial airway, face mask, nasal mask, or the like), and then flows out of the breathing gas circuit, where it is measured by the flow sensing means placed in this flow path. Functionally, the patient's breathing attachment is connected, via the patient's wye, to an artificial atmosphere (either at or above the ambient atmospheric pressure), the oxygen concentration of which is determined by the setting from the plurality of gas sources. From the patient's reference point, the breathing gas circuit is not closed as it is for the pressure triggering strategy, but is open, as provided for by the preinspiratory continuous flow of breathing gas. At the moment that the patient initiates an inspiratory effort and immediately thereafter, the flow past the patient wye will exceed the flow through the breathing attachment. Thus, in the flow triggering system, breathing gas flows with no delay into the patient's breathing attachment the moment that the inspiratory effort begins. In contrast, in the pressure triggering system flow through the patient's breathing attachment from the ventilator is delayed until the pressure threshold is attained and the ventilator senses this event, thereafter causing the flow source means to deliver flow into the breathing gas circuit.

The flow triggering method of the present invention may be implemented in the following preferred embodiment: The predetermined preinspiratory flow of gas that enters the breathing gas circuit from the flow source means is preferably greater than the magnitude of the flow through the patient's breathing attachment, which is the actual threshold flow signal that causes the ventilator to cycle on and deliver the pressure supported breath. Preferably, the predetermined flow into the breathing gas circuit should exceed the value of the flow which results from the patient's inspiratory effort and which triggers the ventilator to cycle on and deliver the pressure-supported breath. With this design, the patient's breathing gas circuit functions as an open continuous flow system until and after the patient's inspiratory effort generates the flow triggering signal.

A benefit of the present invention is that the pressure in the breathing circuit during the early exhalation phase may be kept low to limit the problems encountered when the patient tries to exhale against an artificially high back pressure due to high continuous flow. This feature improves the ability of the respirator to reduce the work of exhalation and still provide an elevated pressure in the patient's airway for breath support, to allow the practitioner to manage the work of initiating a breath and supporting the early phases of the breath.

The flow triggering method of the invention is preferably used in triggering patient initiated breath support routines, such as those known in the art as pressure support, pressure control ventilation (PVC), and its variants with volume priority or guarantee and inverse ratio ventilation; airway pressure release ventilation (APRV) and its variants BIPAP and synchronized APRV; proportional assist ventilation (PAV); and volume priority pressure support ventilation, and the like.

Another benefit of the present invention is its ability to more efficiently deal with leaks in the patient and ventilator system. Leaks are a problem often encountered in pressure triggered ventilation systems. Leaks in the patient and ventilator system are quite common, making it difficult to maintain pressure in the breathing gas circuit. These leaks may be external to the patient, such as those in the tubing connections from the ventilator to the patient, or internal, such as those leaks in the patient physiology. Leaks with pediatric patients are common due to the use of uncuffed endotracheal tubes, which do not form a tight seal with the patient's airway. Whatever the source, the leak can cause false pressure triggering of breaths, as the drop in pressure is interpreted as a patient inspiratory effort. To prevent false pressure triggering, sensitivity may be reduced, unfortunately making pressure triggering even more difficult for a patient once the leak has been eliminated (e.g., the closing of a physiologic leak). On the other hand, leaks encountered during flow triggering can be corrected without impairment of sensitivity because precise control of flow is an inherent component of the flow triggering strategy. In addition, changes in the flow trigger level do not affect sensitivity to the same extent as do changes to the pressure trigger level.

From the above, it will be evident to those skilled in the art that flow triggering of ventilator supported patient breaths from a continuous flow system provides important advantages over previous patient ventilation systems. Other aspects and advantages of the invention will become apparent from the following detailed description and the accompanying drawings, which illustrate by way of example the features of the invention.

BRIEF DESCRIPTION OF THE DRAWINGS

FIG. 3a shows a graph of pressure measurements over time for a typical pressure triggered, pressure supported breath;

FIG. 3b shows a graph of flow measurements over time for a typical pressure triggered, pressure supported breath;

FIG. 5a is an illustration of the patient flow during a single patient breath in a conventional system.

FIG. 5b is an illustration of the flow delivered by the ventilator using the exhalation flow reduction scheme of the present invention.

DETAILED DESCRIPTION OF THE PREFERRED EMBODIMENTS

Figure 1:
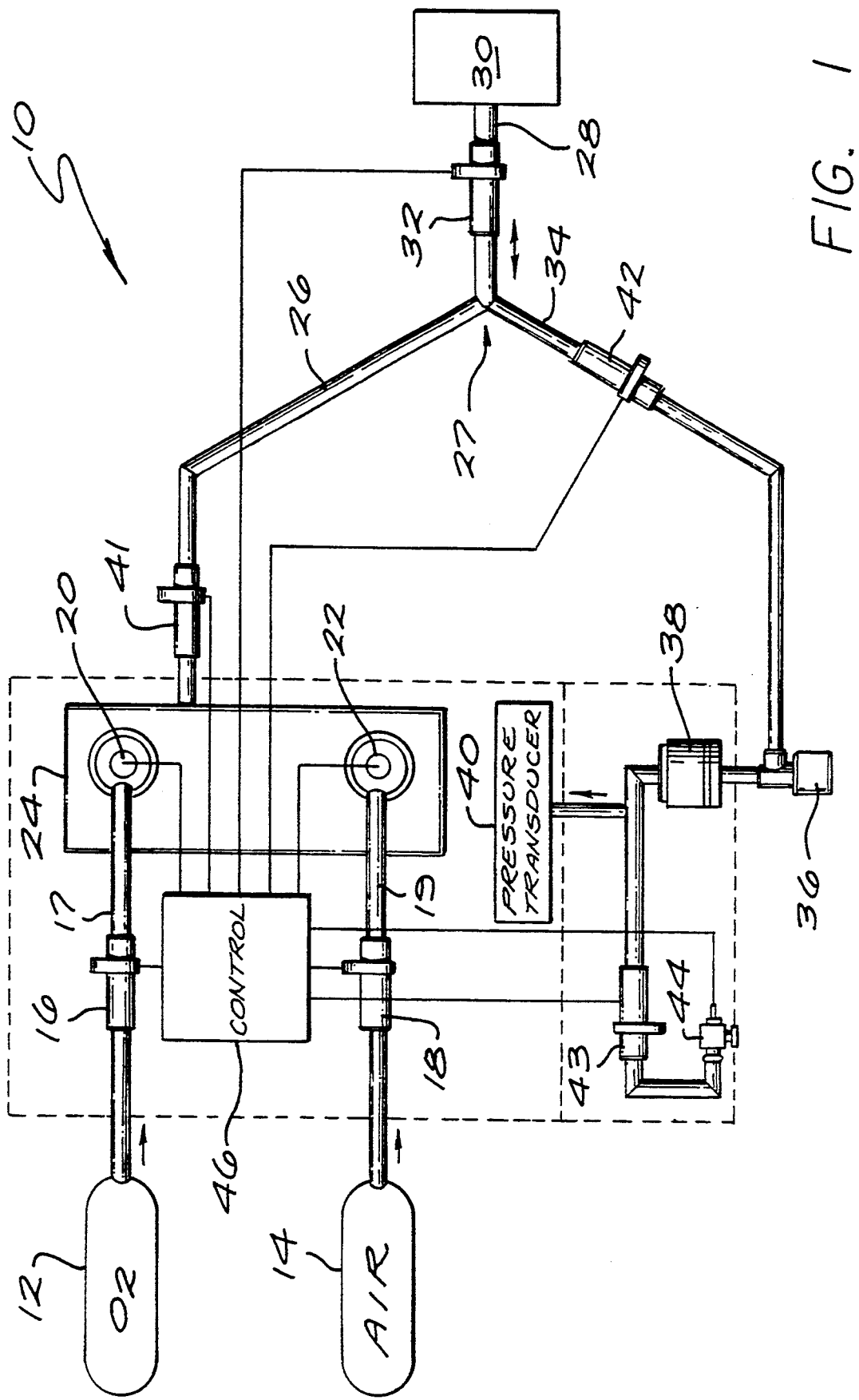
FIG. 1 is a schematic diagram of a flow triggered, open circuit ventilation system.

As is shown in the drawings, which are included for purposes of illustration and not by way of limitation, the invention is embodied in a system for flow triggering a breath support ventilation system which reduces the patient work of breathing, provides improved triggering of the ventilator supported breaths, and allows improved management of the volume and pressure support during a breath. The flow triggering system can be used in patient ventilation systems having a source of breathing gas for a patient, a flow path communicating with the patient, and flow sensor means for measuring the gas flow to and from the patient. The breathing gas source provides a predetermined, preinspiratory, continuous rate of flow of breathing gas to the patient and the flow sensors measure the rate of gas flow to and from the patient. The system determines the difference between the measured flow rate from the patient and the predetermined rate of delivered gas flow to the patient. The system then generates pressure and/or volume support in a desired breath support routine in the flow of gas delivered to the patient when the difference between the flows to and from the patient equals a predetermined threshold or trigger value. The breathing gas may be enriched with a higher concentration of oxygen than normal air. The source of breathing gas may include more than one individual gas source and may also include a device for mixing and controlling the proportions of the individual gases. The system also preferably includes means for determining when exhalation occurs, so that breath support may be discontinued until it is again triggered.

In accordance with the present invention, there is provided a method for flow triggering of breath support for a patient from open ventilation system having a source means of breathing gas, a flow path means for the breathing gas in fluid communication with a patient, and flow sensor means for measuring the rates of gas flow in the flow path. The method comprises delivering a predetermined, continuous rate of flow of the breathing gas from the breathing gas source to the patient prior to breath initiation; measuring the rates of gas flow in the ventilation flow path due to inhalation; generating pressure and/or volume support in the desired breath support routine in the flow of gas delivered to the patient when the rate of gas flow due to inhalation equals a predetermined threshold value; termination of the breath support when the patient initiates an expiratory effort, or when flow in to his or her breathing attachment declines to a predetermined level; and means to reestablish the predetermined continuous rate of flow of the breathing gas from the source to the patient prior to initiation of the next breath.

The present invention also provides for a system for flow triggering of breath support ventilation for use in a functionally open ventilation system having a source means of breathing gas, a flow path means for the breathing gas in fluid communication with a patient breathing attachment, and flow sensor means for measuring the rate of gas flow in the flow path. The system includes means for delivering a predetermined, preinspiratory, continuous rate of flow of the breathing gas from the source to the patient breathing attachment; means for measuring the gas flow in the flow path due to inhalation; means for generating pressure and/or volume support in the desired breath support routine in the flow of gas delivered to the patient breathing attachment when the gas flow due to inhalation equals a predetermined threshold value; means for terminating the breath support when the patient initiates an expiratory effort or when flow into his or her breathing attachment declines to a predetermined level; and means to reestablish the predetermined, preinspiratory, continuous rate of flow of breathing gas during the exhalation interval.

FIG. 1 is a schematic of a present system for flow triggering ventilation according to the present invention. In the currently preferred embodiment, the system 10 includes a source of oxygen gas ($O_2$) 12, which is typically a pressurized tank of oxygen, and a source of air 14, which may also consist of a high pressure tank of air. The sources of air 14 and oxygen 12 may also typically include pressure regulators. The air supply source may also comprise an air compressor which supplies air taken from the ambient atmosphere. Other conventional sources of pressurized oxygen and air in hospital or patient care settings would also be appropriate.

The source of oxygen is connected to a flow meter 16 in the oxygen line 17, and a similar flow meter 18 for the air source 14 is provided in the air line 19. The oxygen line 17 delivers oxygen to its proportional solenoid valve 20, and the air line 19 similarly delivers air to its proportional solenoid valve 22, the two valves releasing oxygen and air for mixing in the mixing chamber 24.

Valves other than proportional solenoid valves and mixing means other than mixing chamber 24 may also be appropriate. The mixed gas is delivered from mixing chamber 24 through the airway conduit 26 to the patient wye fitting 27, which is connected to the patient breathing attachment 30 by breathing tube 28. The breathing attachment 30 may be simplified or replaced by other breathing means in certain implementations. In these implementations the breathing gas flow may be delivered to the patient by means of a breathing tube (artificial airway) or by a breathing mask or other means for delivering breathing gas to the patient's trachea. In either implementation and prior to and immediately after the inspiratory flow, flow meters 16 and 18 monitor the flow of gas to the patient during the continuous flow of gas from the oxygen and air sources (up to and including the time at which the patient's inspiratory flow equals the triggering threshold flow signal) and during exhalation. Exhalation gas from the patient area flows through the exhalation conduit 34 and exhalation flow meter 43. The difference between the sum of flow meters 16 and 18, and exhalation flow meter 43 provides a measurement of flow of breathing air inhaled by the patient from the continuous flow of breathing gas delivered to the patient from the oxygen and air source means. To assist control of the delivery of breathing gas to the patient, the flow control algorithm may monitor flow sensors 16, 18, and 43. During operation of the flow triggering phase and for the restoration of the preinspiratory, continuous flow during exhalation and prior to the patient's next inspiration, flow sensors 16, 18, and 43 become primary inputs to the flow control algorithm prior to the initiation of the inspiratory effort, immediately after the inspiratory effort, and during exhalation when the preinspiratory, continuous flow is being reestablished.

Beginning with and immediately after the patient's inspiratory effort, the flow of breathing gas to the patient will exceed the flow of breathing gas from the patient, and the difference between the flow to and from the patient is compared with a predetermined, "flow trigger" threshold level. This measurement of flow inhaled by the patient is preferably used for triggering the initiation of a breath support routine, such as pressure supported inspiration. Other preferred patient initiated types of breath support routines with which the flow triggering method of the invention may be beneficial include those known in the art as pressure control ventilation (PVC), and its variants with volume priority or guarantee and inverse ratio ventilation; airway pressure release ventilation (APRV) and its variants BIPAP and synchronized APRV; proportional assist ventilation (PAV); and volume priority pressure support ventilation, and the like.

In a preferred embodiment, prior to return of the exiting or exhalation gases to the ambient atmosphere, said gases are passed through a fluid collector vial 36 and a heated bacteria filter 38 provided in the exhalation conduit line. A pressure transducer 40 for measuring the pressure during both inspiration and exhalation may also be provided in the exhalation conduit 34. The system may also include an exhalation valve 44 to close the system to allow breaths and to open the system for exhalation to the atmosphere, to thereby return the filtered and cleaned exiting gas to the atmosphere from the open ventilator system.

The invention may use other methods for measuring the inhaled flow by the patient from the preinspiratory, continuous flow of breathing gas. A flow meter 32 may be placed between the patient wye 27 and the patient breathing attachment 30 to measure patient inhalation flow directly. Alternatively, or in addition to flow meter 32, a delivery flow meter 41 may be provided in the airway conduit 26 for measuring the flow of mixed breathing gas delivered to the patient, and an exhalation flow meter 42 may be installed in the exiting airway conduit 34 for monitoring the flow of gas from the patient during inspiration effort and exhalation. The difference between flow meters 41 and 42 also provides a measurement of flow inhaled by the patient from the preinspiratory, continuous flow of breathing gas from the source means.

It will be understood by those skilled in the art that any combination of signals from flow meters 16, 18, 32, 41, 42, and 43 may be used for sensing and measuring the flow inhaled by the patient for use as a flow trigger signal for inspiration.

An electronic control means 46, preferably including a microprocessor for controlling all of the functions of the ventilator control system, is connected to the oxygen source flow meter 16, the air source flow meter 18, the oxygen proportional solenoid valve 20, the air proportional solenoid valve 22, the patient exhalation flow meter 43, and any additional flow meters (41) in the inspiration airway conduit 26, the patient wye flow meter 32, or flow meters (42) in the exiting or exhalation airway conduit 34. Electronic control means 46 compares the rate of flow to the patent through the patient wye 27 as derived by any of the previously discussed means, with a predetermined flow threshold level to detect whether the patient's inspiratory effort has met the criterion for triggering pressure support by operation of the proportional solenoid valves 20, 22. The control means 46 also controls the proportional mixing through the proportional solenoid valves 20, 22, and operates to open the exhalation valve 44 and cause the proportional solenoid valves 20, 22 to discontinue pressure support when the exhalation effort of the patient is detected, returning the flow of breathing gas to the patient to the preinspiratory level of continuous flow in readiness for the patient's next inspiratory effort.

The flow triggering of breaths involves monitoring the flow of inhaled gas from the continuous flow of breathing gas delivered to the patient, which reduces the energy required from the patient to initiate a ventilator breath, and in a preferred embodiment further involves commencement of inspiratory pressure support when the patient's inspiratory flow meets the triggering criterion. The continuous, minimal flow of breathing gas delivered into the breathing circuit prior to the initiation of the inspiratory effort serves two functions: First, the continuous flow converts the normally closed breathing gas circuit into one that is functionally open. Second, the continuous flow establishes a highly stable flow of breathing gas which can be monitored by the flow sensing means to determine when the patient begins his or her inspiratory effort. This flow triggering approach converts the initial work of inspiration from an essentially isometric effort to a quasi-isotonic effort. Both the level of continuous flow and the required change in flow due to inhalation for inspiratory support triggering may be adjusted through the control means.

As previously discussed, the energy expended by a patient while breathing on a mechanical ventilator can be divided into two components. The first component is the energy required to trigger the ventilator to begin the inspiration. The second component is the energy required to maintain adequate gas flow once the ventilator has been triggered to deliver inspiratory support.

A primary purpose of a pressure support mode of breath support ventilation is to reduce the second energy component. This is accomplished by providing a positive pressure level during the inspiratory phase of the breath. This positive pressure may be used to reduce or negate the imposed work due to the resistance of the artificial airway, and/or the resistance and compliance intrinsic to the patient's respiratory system. In extremely weak patients, the application of pressure support can provide sufficient tidal volumes without using assist-control ventilation, and can thereby increase patient comfort while returning to the patient some measure of control over his or her breathing pattern. Patients have been shown to expend less work or energy in breathing when pressure support is used. This can have important implications when weaning patients from the ventilator, since the patient must then be progressively strengthened to breath without the pressure support to inspiration. As mentioned above, other types of breath support may also be advantageously employed with the flow triggering method of the invention.

Figure 2A:
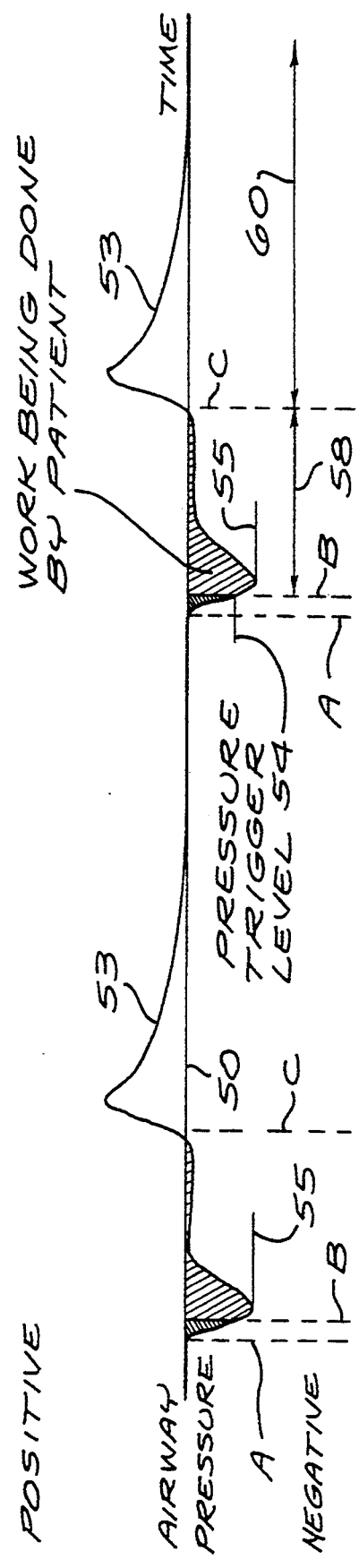
FIG. 2a shows a graph of pressure measurements over time for a typical pressure triggered breath without pressure support.
Figure 2B:
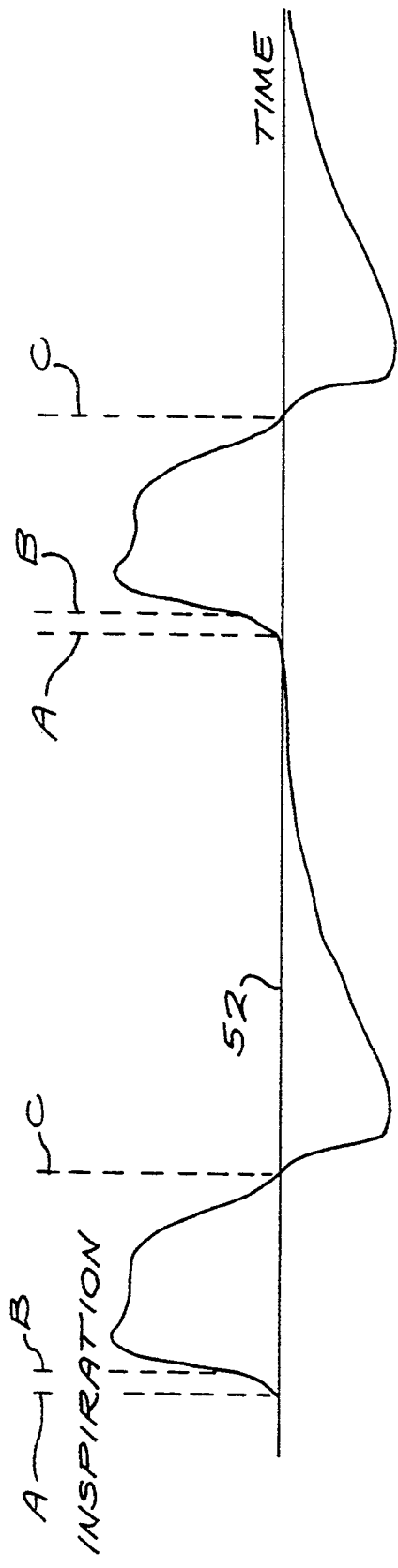
FIG. 2b shows a graph of flow measurements over time for a typical pressure triggered breath without pressure support.

FIGS. 2a and 2b show traces of pressure over time and flow over time, respectively, as they vary from the patient pressure baseline 50 (FIG. 2a) and the patient flow baseline 52 (FIG. 2b) for a typical spontaneous, non-pressure supported, ventilator delivered breath. In FIG. 2a, the area under pressure-time trace 53 which is below the pressure baseline 50 represents the work being done by the patient. The portion of the curve 53 in the pressure-time trace between point A and point B at the pressure trigger level 54 depicts the portion of this work required to trigger inspiratory support. The portion of the curve between points B and C represents the remaining work of inhalation 58 required to maintain an adequate gas flow to satisfy the inspiratory demands of the patient. In other terms, the area between B and C represents the work required of the patient to sustain the breath. Note (with respect to the pressure baseline 50) that, as shown in FIG. 2a, the pressure is negative throughout inspiration, indicating that the patient is performing work during this entire period. It should also be noted that the peak negative pressure required of the patient is the level 55 noted on FIG. 2a. The exhalation phase 60 begins at the end of the inhalation phase. FIG. 2b shows the flow rates corresponding to the pressure-time curves of FIG. 2a. It is evident that the flow prior to B, the point at which the pressure triggering is effecting is very low and that substantial work is still performed by the patient between B and C, even though the pneumatic system was cycled on at B.

FIGS. 3a and 3b show traces of pressure over time about a patient pressure baseline 62, and flow over time about a flow baseline 64, respectively, for a typical pressure triggered, pressure-supported breath. Once the breath is triggered at B representing the pressure trigger level 66, the ventilator creates a positive pressure to reduce the patient's work of inspiration. Prior to the inspiration cycle 68, a negative pressure, and therefore an expenditure of energy by the patient, is required to trigger the breath. Pressure support is discontinued when the patient exerts an expiratory effort or when flow into his/her lungs declines to a preselected value. At this point, the patient begins the exhalation phase 70. It may be seen that the flow level at the time of triggering 72 was relatively low, but rapidly increased in response to the pressure support supplied after pressure triggering. However, there remains a substantial amount of work which must be expended by the patient for this scheme as well.

Figure 4A:
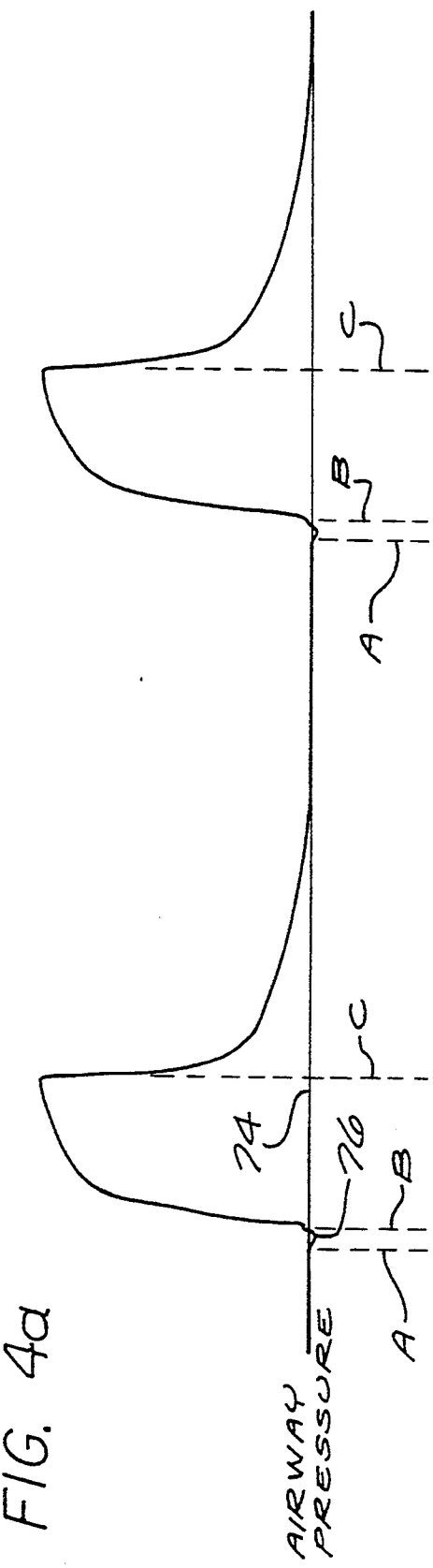
FIG. 4a shows a graph of pressure measurements over time for a typical flow triggered, pressure supported breath.
Figure 4B:
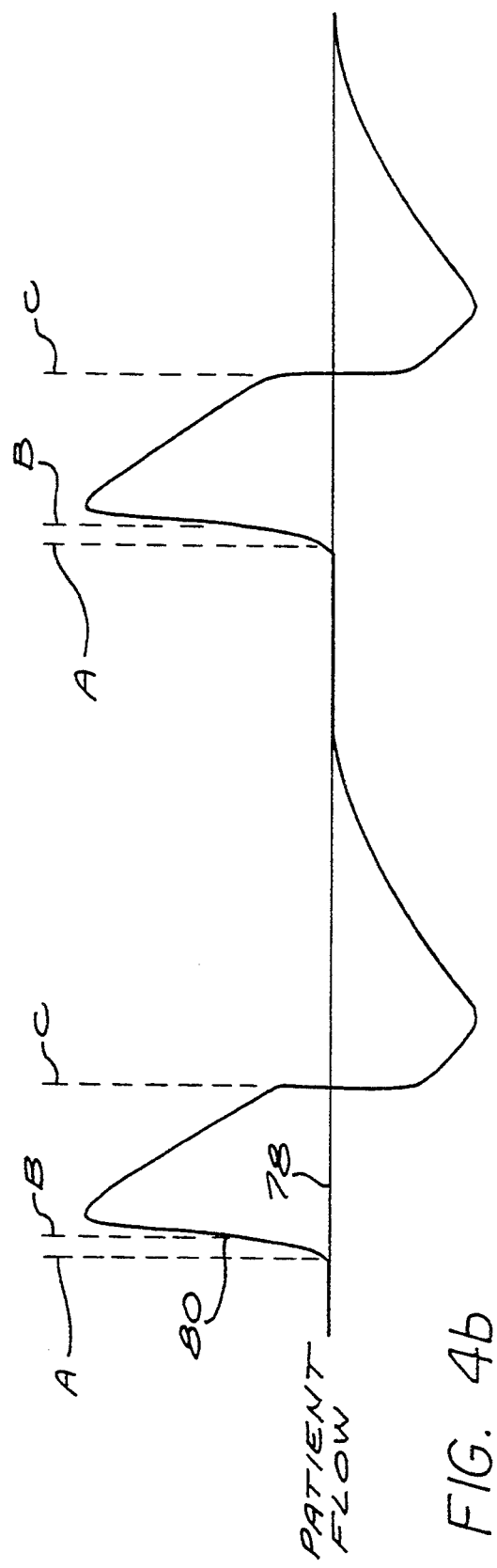
FIG. 4b shows as graph of flow measurements over time for a typical flow triggered, pressure supported breath.

As illustrated in FIGS. 4a and 4b, the present invention's combination of flow triggering with pressure support (with an appropriate selection of the support pressure) can reduce the energy expenditure by the patient to a virtually negligible level.

FIGS. 4a and 4b show traces of pressure over time about a patient pressure baseline 74, and flow over time about a flow baseline 78, respectively, for a typical, flow triggered, pressure-supported breath according to one embodiment of the present invention. Comparison of FIGS. 3a and 4a shows that the pressure 66 required for pressure triggering is more negative compared with the pressure 76 resulting from flow triggering. The negative pressure component 66 (in the pressure triggering example of FIG. 3), representing the work done by the patient, is substantial, whereas the negative component 76 (with flow triggering example, FIG. 4) is minor. The flow 80 to the patient can be seen to be higher at the flow trigger level in the flow triggered system of FIG. 4b than the flow level 72 in the pressure triggered system of FIG. 3b. With respect to the flow triggering traces in FIG. 4, both the less negative triggering pressure and the higher inspiratory flows early in the breath, compared to the pressure triggered traces of FIG. 3 result from the physical differences between the flow systems. In the flow triggered case, the patient inhales from a functionally open system (i.e., the patient's earliest flow demands are met by the preinspiratory, continuous flow), whereas in the pressure triggered case, the patient inhales from a closed system (i.e., the patient receives no flow until the pressure trigger threshold is reached). Thus, it can be seen that the combination of flow triggering with pressure support of the present invention reduces the energy expended by the patient to trigger inspiratory support and also reduces the patient energy required to maintain the inspiratory phase. Thus, by combining flow triggering with pressure support according to the present invention, the work done by the patient to trigger pressure-supported breathing is minimized while the appropriate selection of the support pressure allows the patient's inspiratory work to be set at a desired level. From the above, it may be seen that the work associated with the interval A-B in FIGS. 2 and 3 may be substantially reduced with the present invention as illustrated by the interval A-B of FIG. 4. Thus, while the patient work of FIG. 3 is lower than that of FIG. 2, representing the difference between pressure triggering of flow support and pressure triggering of pressure support, the latter representing a more aggressive technique for support to a pressure triggered system. The present invention further minimizes the patient work compared to these previous strategies.

While pressure support of ventilation has a number of advantages as discussed above, the attendant high pressures in the exhalation limb of the patient's breathing gas circuit during the exhalation phase of the flow triggered pressure supported breath can be a cause of concern for the patient unless they are carefully controlled. Pressures above the PEEP (baseline pressure value) generally indicate that the patient's lungs are hyperinflated. These events can place the patient's diaphragm and accessory inspiratory muscles in a position of relative inefficiency and may impose a higher work of breathing on the patient. An alert patient may also attempt to forcefully exhale to PEEP (baseline pressure value), which also adds extra work to the breathing effort. Thus it would be desirable to maintain the lowest possible pressures in the patient breathing circuit during exhalation. A long recognized disadvantage of the earlier developed, continuous flow concept was the presence, in the exhalation limb of the patient's breathing gas circuit, of the practitioner selected, continuous flow in addition to the patient's own exhalation flow. This constant extra flow elevated the pressure in the patient's breathing gas circuit (during exhalation), which could also lead to problems similar to those discussed above.

The present invention of flow triggering can be configured to minimize this extra, non-patient generated exhalation flow in the patient's breathing gas circuit. According to a preferred embodiment of the invention, when the ventilator declares exhalation and (opens the exhalation valve) the preinspiratory, continuous flow of breathing gas is set to a minimal value. This minimal value is maintained throughout the most active phase of the patient's exhalation, then it is reset by the ventilator to the specified value for the preinspiratory, continuous flow of breathing gas, in anticipation of the next inspiratory effort.

FIG. 5 illustrates the function of this preferred embodiment. FIG. 5a illustrates the patient flow above and below baseline in a system of pressure supported breathes as previously described. FIG. 5b illustrates the flow support time history delivered by this preferred embodiment, in which the flow is reduced during the early exhalation period and then returned to the practitioner selected continuous base flow. By using this scheme, the over-pressurization of the patient's airway is avoided during the early period exhalation, thus reducing the work performed by the patient and limiting the undesirable effects described above.

It may be seen from the foregoing description that the system and method of the present invention allow for reduction of patient discomfort and work of ventilator supported breathing by maintenance of a preinspiratory, continuous flow of breathing gas to the patient and by flow triggering of inspiratory support. In combination with breath support to the patient during the inspiration effort, the flow triggering strategy of the invention offers significant improvements in providing breath support to patients having weakened respiratory capabilities.

Although a specific embodiment of the invention has been described and illustrated, it is clear that it is susceptible to numerous modifications and embodiments within the ability of those skilled in the art and without the exercise of the inventive faculty. Thus, it should be understood that various changes in form, detail and application of the present invention may be made without departing from the spirit and scope of this invention.

We claim:

1. A method of flow triggering of breath support ventilation to a patient supplied with a predetermined, preinspiratory, continuous flow of breathing gas from a ventilation system having a source of breathing gas, a patient breathing attachment, an exhalation valve, and a functionally open breathing gas flow path in fluid communication with said source of breathing gas, said ventilation flow path including flow sensor means for measuring flow rate of said breathing gas from said patient breathing attachment to said exhalation valve, the steps of the method comprising:

delivering said predetermined rate of flow of said breathing gas from said source to said patient breathing attachment;

measuring said flow rate of breathing gas from said source of breathing gas to said patient breathing attachment to determine a gas supply flow rate;

measuring said flow rate of breathing gas from said patient attachment to said exhalation valve to determine an exiting gas flow rate;

determining patient inspiratory effort in said flow path by comparing said gas supply flow rate with said exiting gas flow rate, and determining a flow rate change due to patient inhalation or exhalation, thereby indicating the patient's breathing efforts;

generating breath support in said delivered flow of gas when said flow rate change exceeds a predetermined threshold value; and restoring delivery of said breathing gas from said source to said patient breathing attachment at said preinspiratory, continuous rate of flow before a patient's next inspiratory effort.

2. The method of claim 1, wherein said source of breathing gas comprises a plurality of different gas sources, and further comprises the step of mixing said plurality of different gases.

3. The method of claim 2, further comprising the step of controlling the mixing of said different gas sources according to a predetermined proportion of said different gases.

4. The method of claim 1, wherein said ventilation flow path includes an inhalation and exhalation flow path into and from said patient breathing attachment, and said inhalation flow path and said exhalation flow path form a wye junction communicating with the patient breathing attachment, and the step of determining the rate of gas flow in said flow path comprises measuring gas flow at the portion of the patient wye junction communicating with the patient breathing attachment.

5. The method of claim 1, wherein said ventilation flow path includes an exhalation flow path from said patient breathing attachment and an inhalation flow path to the patient breathing attachment, and the step of determining the rate of gas flow into and from said patient breathing attachment comprises performing measurements at least one position in the inhalation flow path and at least one position in the exhalation flow path.

6. The method of claim 1, wherein said flow path includes an exhalation flow path from said patient breathing attachment, and said measurement of said change in the rate of gas flow in said flow path is measured in at least one location in said exhalation flow path.

7. The method of claim 1, wherein said ventilation flow path includes a plurality of flow sensor means and a control means for measuring the change in the rate of gas flow, and said step of measuring said change in the rate of gas flow comprises measurement at least one of the sensor means.

8. A system of flow triggering breath support ventilation to a patient supplied with a predetermined, preinspiratory, continuous flow of breathing gas, comprising a ventilation system having a source of breathing gas, a patient breathing attachment, an exhalation valve, and a functionally open breathing gas flow path in fluid communication with said source of breathing gas, said patient breathing attachment and said exhalation valve, and flow sensor means for measuring flow rate of said breathing gas from said patient breathing attachment to said exhalation valve, the system further comprising:

means for delivering said breathing gas from said source to said patient breathing attachment at said predetermined, continuous rate of flow;

flow sensor means in said flow path for measuring flow rate of said breathing gas from said source of breathing gas to said patient breathing attachment to determine a gas supply flow rate, and for measuring flow rate of said breathing gas from said patient breathing attachment to said exhalation valve to determine an exiting gas flow rate;

means responsive to said flow sensor means for determining patient breathing efforts by comparing said gas supply flow rate with said exiting gas flow rate to determine a flow rate change due to patient inhalation or exhalation efforts, means for generating breath support in said delivered flow of gas when said flow rate change exceeds a predetermined threshold value; and means for restoring delivery of said breathing gas from said source to said patient breathing attachment at said preinspiratory, continuous rate of flow before a next patient's inspiratory effort.

9. The system of claim 8, wherein said source of breathing gas comprises a plurality of different gas sources, and means for mixing said gas from said different gas sources.

10. The system of claim 8, further including means for controlling the proportions in said mixture of said gas from said different gas sources.

11. The system of claim 8, wherein said ventilation flow path includes an inhalation and exhalation flow path into and from said patient breathing attachment, and said source of inhalation and exhalation flow paths form a wye junction communicating with the patient breathing attachment, and wherein said flow sensor means for measuring the rate of gas flow into said patient breathing attachment is located at said wye junction.

12. The system of claim 11, wherein said flow sensor means is located in the ventilation flow path between said wye junction and said patient breathing attachment.

13. The system of claim 8, wherein said ventilation flow path includes an exhalation flow path from said patient breathing attachment, an inhalation flow path to said patient breathing attachment, and said flow sensor means for determining the change in the rate of gas flow into and from said patient breathing attachment comprises at least one flow sensor located in at least one location in said exhalation flow path and at least one other flow sensor in at least one other location in said inhalation flow path.

14. The system of claim 8, further comprising a plurality of flow sensor means and a control means for measuring the gas flow rate at least one of the flow sensor means.

15. The system of claim 8, further comprising means to determine the beginning of a patient's exhalation cycle and means to reduce the flow rate for a predetermined period of time at the beginning of said exhalation cycle.

* * * * *